(12) United States Patent
Liu et al.

(10) Patent No.: US 10,427,110 B2
(45) Date of Patent: Oct. 1, 2019

(54) CHEMICALLY AND UV CROSS-LINKED HIGH SELECTIVITY POLYIMIDE MEMBRANES FOR GAS SEPARATIONS

(71) Applicant: UOP LLC, Des Plaines, IL (US)

(72) Inventors: Chunqing Liu, Arlington Heights, IL (US); Howie Q. Tran, Skokie, IL (US)

( * ) Notice: Subject to any disclaimer, the term of this patent is extended or adjusted under 35 U.S.C. 154(b) by 159 days.

(21) Appl. No.: 15/798,346

(22) Filed: Oct. 30, 2017

(65) Prior Publication Data

US 2018/0050310 A1    Feb. 22, 2018

Related U.S. Application Data

(63) Continuation of application No. PCT/US2016/037745, filed on Jun. 16, 2016.

(60) Provisional application No. 62/184,537, filed on Jun. 25, 2015.

(51) Int. Cl.

| | | |
|---|---|---|
| *B01D 71/64* | (2006.01) | |
| *C08G 73/10* | (2006.01) | |
| *C01B 32/50* | (2017.01) | |
| *B01D 53/22* | (2006.01) | |
| *B01D 67/00* | (2006.01) | |
| *C01B 23/00* | (2006.01) | |
| *C02F 1/44* | (2006.01) | |
| *C07C 7/144* | (2006.01) | |
| *C07C 29/76* | (2006.01) | |
| *C10G 31/00* | (2006.01) | |
| *C10L 3/10* | (2006.01) | |
| *B01D 69/12* | (2006.01) | |
| *C02F 101/30* | (2006.01) | |
| *B01D 69/06* | (2006.01) | |

(52) U.S. Cl.
CPC .......... *B01D 71/64* (2013.01); *B01D 53/228* (2013.01); *B01D 67/0013* (2013.01); *B01D 69/125* (2013.01); *C01B 23/0047* (2013.01); *C01B 32/50* (2017.08); *C02F 1/44* (2013.01); *C07C 7/144* (2013.01); *C07C 29/76* (2013.01); *C08G 73/10* (2013.01); *C08G 73/106* (2013.01); *C08G 73/1042* (2013.01); *C08G 73/1064* (2013.01); *C08G 73/1067* (2013.01); *C10G 31/00* (2013.01); *C10L 3/101* (2013.01); *C10L 3/103* (2013.01); *C10L 3/104* (2013.01); *B01D 69/06* (2013.01); *B01D 2323/30* (2013.01); *B01D 2323/345* (2013.01); *C02F 2101/30* (2013.01); *C10G 2400/02* (2013.01); *C10G 2400/04* (2013.01); *C10L 2290/548* (2013.01)

(58) Field of Classification Search
CPC .............. B01D 53/228; B01D 67/0013; B01D 69/125; B01D 71/64; B01D 2323/30; B01D 2323/345; C08G 73/1042; C08G 73/106; C08G 73/1064; C08G 73/1067; C07C 7/144; C10L 3/104; C01B 32/50
See application file for complete search history.

(56) References Cited

U.S. PATENT DOCUMENTS

| | | | |
|---|---|---|---|
| 5,663,287 A * | 9/1997 | Oka | C08G 73/1042 528/350 |
| 5,762,798 A | 6/1998 | Wenthold et al. | |
| 6,932,589 B2 | 8/2005 | Suzuki | |
| 7,048,846 B2 | 5/2006 | White et al. | |
| 7,485,173 B1 | 2/2009 | Liu et al. | |
| 8,337,598 B2 | 12/2012 | Yates et al. | |
| 8,613,362 B2 | 12/2013 | Liu et al. | |
| 2005/0268783 A1 | 12/2005 | Koros et al. | |
| 2010/0167208 A1* | 7/2010 | Wang | C08G 73/106 430/287.1 |
| 2010/0269698 A1* | 10/2010 | Yates | B01D 53/228 96/10 |
| 2012/0322911 A1* | 12/2012 | Liu | B01D 53/228 522/164 |

(Continued)

FOREIGN PATENT DOCUMENTS

WO    2015047702 A1    4/2015

OTHER PUBLICATIONS

Search Report dated Sep. 22, 2016 for corresponding PCT Appl. No. PCT/US2016/037745.

*Primary Examiner* — Jason M Greene

(57) ABSTRACT

This invention discloses a membrane composition, a method of making, and applications for a new type of high selectivity, high plasticization-resistant and solvent-resistant, both chemically and UV cross-linked polyimide membranes. Gas permeation tests on these membranes demonstrated that they not only showed high selectivities, but also showed extremely high $CO_2$ plasticization resistance under $CO_2$ pressure up to 4923 kPa (700 psig). This new type of high selectivity, high plasticization-resistant and solvent-resistant, both chemically and UV cross-linked polyimide membranes can be used for a wide range of gas separations such as separations of $H_2/CH_4$, $He/CH_4$, $CO_2/CH_4$, $CO_2/N_2$, olefin/paraffin separations (e.g. propylene/propane separation), $O_2/N_2$, iso/normal paraffins, polar molecules such as $H_2O$, $H_2S$, and $NH_3$ mixtures with $CH_4$, $N_2$, $H_2$, and other light gases separations. The membranes can also be used for liquid separations such as in the removal of organic compounds from water.

22 Claims, No Drawings

(56) References Cited

U.S. PATENT DOCUMENTS

2014/0130667 A1* 5/2014 Sano .................... B01D 53/228
95/51
2015/0165383 A1 6/2015 Liskey et al.
2017/0333836 A1* 11/2017 Kodama .............. B01D 53/228

* cited by examiner

CHEMICALLY AND UV CROSS-LINKED HIGH SELECTIVITY POLYIMIDE MEMBRANES FOR GAS SEPARATIONS

CROSS-REFERENCE TO RELATED APPLICATIONS

This application is a Continuation of copending International Application No. PCT/US2016/037745 filed Jun. 16, 2016 which claims benefit of U.S. Provisional Application No. 62/184,537 filed Jun. 25, 2015, now expired, the contents of which cited applications are hereby incorporated by reference in their entirety.

BACKGROUND OF THE INVENTION

Membrane-based technologies have advantages of both low capital cost and high-energy efficiency compared to conventional separation methods. Polymeric membranes have proven to operate successfully in industrial gas separations such as in the separation of nitrogen from air and the separation of carbon dioxide from natural gas. Cellulose acetate (CA) is a polymer currently being used in commercial gas separation. For example, UOP LLC's Separex™ CA membrane is used extensively for carbon dioxide removal from natural gas. Nevertheless, while they have experienced commercial success, CA membranes still need improvement in a number of properties including selectivity, permeability, chemical and thermal stability. Natural gas often contains substantial amounts of heavy hydrocarbons, aromatics, and water, either as an entrained liquid, or in vapor form, which may lead to condensation within membrane modules. The gas separation capabilities of polymeric membranes are affected by contact with liquids including hydrocarbons and water. The presence of more than modest levels of hydrogen sulfide, especially in conjunction with water and heavy hydrocarbons, is also potentially damaging. Therefore, precautions must be taken to remove the entrained liquid water and heavy hydrocarbons upstream of the membrane separation steps. Another issue of polymeric membranes that still needs to be addressed for their use in gas separations is the plasticization of the polymer by condensable gases such as carbon dioxide and propylene that leads to swelling of the membrane as well as a significant increase in the permeability of all components in the feed and a decrease in the selectivity of the membranes. For example, the permeability coefficient of $CO_2$ in polymeric membranes begins to increase when the pressure is above a certain level due to the onset of plasticization by the $CO_2$. A high concentration of sorbed $CO_2$ leads to increased segmental motion, and, consequently, the transport rate of the penetrant is enhanced. The challenge of treating gas, such as natural gas, that contains relatively large amounts of $CO_2$, such as more than about 50%, is particularly difficult.

Polymeric membrane materials have been found to be useful in gas separations. Numerous research articles and patents describe polymeric membrane materials (e.g., polyimides, polysulfones, polycarbonates, polyethers, polyamides, polyarylates, polypyrrolones, etc.) with desirable gas separation properties, particularly for use in oxygen/nitrogen separation (See, for example, U.S. Pat. No. 6,932,589). The polymeric membrane materials are typically used in processes in which a feed gas mixture contacts the upstream side of the membrane, resulting in a permeate mixture on the downstream side of the membrane with a greater mole fraction of one of the components than the composition of the original feed gas mixture. A pressure differential is maintained between the upstream and downstream sides, providing the driving force for permeation. The downstream side can be maintained as a vacuum, or at any pressure below the upstream pressure.

The membrane performance is characterized by the flux of a gas component across the membrane. This flux can be expressed as a quantity called the permeability (P), which is a pressure- and thickness-normalized flux of a given component. The separation of a gas mixture is achieved by a membrane material that permits a faster permeation rate for one component (i.e., higher permeability) over that of another component. The efficiency of the membrane in enriching a component over another component in the permeate stream can be expressed as a quantity called selectivity. Selectivity can be defined as the ratio of the permeabilities of the gas components across the membrane (i.e., $P_A/P_B$, where A and B are the two components). A membrane's permeability and selectivity are material properties of the membrane material itself, and thus these properties are ideally constant with feed pressure, flow rate and other process conditions. However, permeability and selectivity are both temperature-dependent. It is desired to develop membrane materials with a high selectivity (efficiency) for the desired component, while maintaining a high permeability (productivity) for the desired component.

The relative ability of a membrane to achieve the desired separation is referred to as the separation factor or selectivity for the given mixture. There are however several other obstacles to use of a particular polymer to achieve a particular separation under any sort of large scale or commercial conditions. One such obstacle is permeation rate. One of the components to be separated must have a sufficiently high permeation rate at the preferred conditions or else extraordinarily large membrane surface areas are required to allow separation of large amounts of material. Another problem that can occur is that at conditions where the permeability is sufficient, such as at elevated temperatures or pressures, the selectivity for the desired separation can be lost or reduced. Another problem that often occurs is that over time the permeation rate and/or selectivity is reduced to unacceptable levels. This can occur for several reasons. One reason is that impurities present in the mixture can over time clog the pores, if present, or interstitial spaces in the polymer. Another problem that can occur is that one or more components of the mixture can alter the form or structure of the polymer membrane over time thus changing its permeability and/or selectivity. One specific way this can happen is if one or more components of the mixture cause plasticization of the polymer membrane. Plasticization occurs when one or more of the components of the mixture act as a solvent in the polymer often causing it to swell and lose its membrane properties. It has been found that polymers such as cellulose acetate and polyimides which have particularly good separation factors for separation of mixtures comprising carbon dioxide and methane are prone to plasticization over time thus resulting in decreasing performance of these membranes.

Some new high-performance polymers such as new polyimides (PIs), poly(trimethylsilylpropyne) (PTMSP), and polytriazole exhibit high ideal selectivities for $CO_2$ over $CH_4$ when measured with pure gases at modest pressures in the laboratory. However, the selectivity obtained under mixed gas, high pressure conditions is much lower than the calculated ideal level. In addition, gas separation processes based on glassy solution-diffusion membranes frequently suffer from plasticization of the stiff polymer matrix by the sorbed penetrant molecules such as $CO_2$ or $C_3H_6$. Plasticization of the polymer represented by the membrane structure swelling and a significant increase in the permeabilities of all components in the feed occurs above the plasticization pressure when the feed gas mixture contains condensable gases.

Thus, there is a critical need for new high-performance membranes that will provide and maintain adequate performance under conditions of exposure to organic vapors or liquids, high concentrations of acid gases such as $CO_2$ and hydrogen sulfide, and water vapor that are commonplace in natural gas treatment.

Conventional methods for stabilizing polymeric membranes involve either annealing or cross-linking. Cross-linking is a useful method to suppress the polymer membrane plasticization. Polymer membrane cross-linking methods include thermal treatment, radiation, chemical cross-linking, and UV-photochemical processes. Cross-linking offers the potential to improve the mechanical and thermal properties of a membrane. Cross-linking can be used to increase membrane stability in the presence of aggressive feed gases and to simultaneously reduce plasticization of the membrane. Normally, cross-linked polymer membranes have a high resistance to plasticization, but their other properties such as permeability and selectivity are much less than desired.

US 2005/0268783 A1 disclosed chemically cross-linked polyimide hollow fiber membranes prepared from a monoesterified polymer followed by final cross-linking after hollow fiber formation.

U.S. Pat. No. 7,485,173 disclosed UV cross-linked mixed matrix membranes via UV radiation. The cross-linked mixed matrix membranes comprise microporous materials dispersed in the continuous UV cross-linked polymer matrix.

U.S. Pat. No. 8,337,598 disclosed a thin film composite hollow fiber membrane with a core layer and a UV-cross-linked polyimide polymer sheath layer.

Even after cross-linking of conventional polymers in accordance with the state of the art prior to the current invention, there has remained a need to improve the selectivity and permeability of the resulting membranes.

The present invention provides a new type of high selectivity, high plasticization-resistant and solvent-resistant, both chemically and UV cross-linked polyimide membranes.

SUMMARY OF THE INVENTION

This invention discloses a composition of, a method of making, and applications of a new type of high selectivity, high plasticization-resistant and solvent-resistant, both chemically and UV cross-linked polyimide membranes.

Two main issues for traditional polymeric membranes are relatively low selectivities and plasticization of the polymers by condensable gases such as carbon dioxide and propylene that leads to swelling of the membrane as well as a significant increase in the permeability of all components in the feed and a decrease in the selectivity of the membranes. The present invention discloses a new type of both chemically and UV cross-linked polyimide membranes that have shown high selectivities and also extremely high plasticization resistance to condensable gases such as $CO_2$ and propylene for gas separations.

As an example, single-gas experimental results demonstrated that the both UV physically cross-linked and 3-isocyanatopropyltriethoxysilane chemically cross-linked poly(3,3',4,4'-diphenylsulfone tetracarboxylic dianhydride (DSDA)-3,3',5,5'-tetramethyl-4,4'-methylene dianiline (TMMDA)-3,3'-dihydroxy-4,4'-diamino-biphenyl (HAB)) polyimide polymeric membrane described in this invention showed no plasticization induced by $CO_2$ condensable gas up to 700 psig $CO_2$ partial pressure for $CO_2/CH_4$ separation. The new membrane also showed high selectivities ($\alpha_{CO2/CH4}$=42.5, $\alpha_{H2/CH4}$=245.9, $\alpha_{He/CH4}$=243.4) and permeabilities ($P_{CO2}$=7.22 Barrers, $P_{H2}$=41.8 Barrers, $P_{He}$=41.4 Barrers) for $CO_2/CH_4$, $H_2/CH_4$, and $He/CH_4$ separations.

This new type of high selectivity, high plasticization-resistant and solvent-resistant, both chemically and UV cross-linked polyimide membranes are highly promising for a variety of gas separations such as separations of $H_2/CH_4$, $He/CH_4$, $CO_2/CH_4$, $CO_2/N_2$, olefin/paraffin separations (e.g. propylene/propane separation), $O_2/N_2$, iso/normal paraffins, polar molecules such as $H_2O$, $H_2S$, and $NH_3$ mixtures with $CH_4$, $N_2$, $H_2$, and other light gases separations.

DETAILED DESCRIPTION OF THE INVENTION

Current polymeric membrane materials have reached a limit in their productivity-selectivity trade-off relationship for separations. Another issue is that gas separation processes based on glassy solution-diffusion membranes frequently suffer from plasticization of the stiff polymer matrix by the sorbed condensable penetrant molecules such as $CO_2$ or $C_3H_6$. Plasticization of the polymer is exhibited by swelling of the membrane structure and a significant increase in the permeabilities for all components in the feed occurs above the plasticization pressure when the feed gas mixture contains condensable gases.

For example, for a cellulose acetate membrane, the high solubility of $CO_2$ swells the polymer to such an extent that intermolecular interactions are disrupted. As a result, mobility of the acetyl and hydroxyl pendant groups, as well as small-scale main chain motions, would increase thereby enhancing the gas transport rates. This result indicates a strong need to develop new plasticization-resistant membrane materials. The markets for membrane processes could be expanded considerably through the development of robust, high plasticization-resistant membrane materials.

Conventional methods for stabilizing the polymeric membranes against plasticization are either annealing or cross-linking. Polymeric membrane cross-linking methods include thermal treatment, radiation, chemical cross-linking, UV-photochemical, blending with other polymers, etc.

This invention relates to a new type of high selectivity, high plasticization-resistant and solvent-resistant, both chemically and UV cross-linked polyimide membranes. More specifically, this invention relates to a method for making these novel high selectivity, high plasticization-resistant and solvent-resistant, both chemically and UV cross-linked polyimide membranes. This invention also pertains to the applications of these high selectivity, high plasticization-resistant and solvent-resistant, both chemically and UV cross-linked polyimide membranes for a variety of gas separations such as separations of $CO_2/CH_4$, $H_2/CH_4$, $He/CH_4$, $CO_2/N_2$, olefin/paraffin separations (e.g. propylene/propane separation), $O_2/N_2$, iso/normal paraffins, polar molecules such as $H_2O$, $H_2S$, and $NH_3$/mixtures with $CH_4$, $N_2$, $H_2$, and other light gases separations.

The new type of high selectivity, high plasticization-resistant and solvent-resistant, both chemically and UV cross-linked polyimide membranes described in the present invention is formed from a new polyimide polymer with a plurality of repeating units of formula (I):

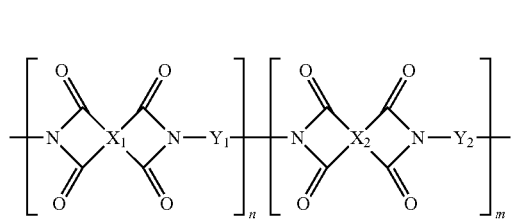
(I)

wherein $X_1$ is selected from the group consisting of

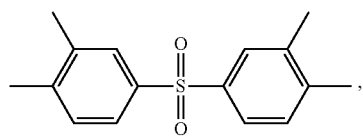

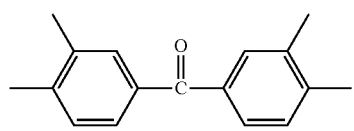

and mixtures thereof; wherein $X_2$ is selected from the group consisting of

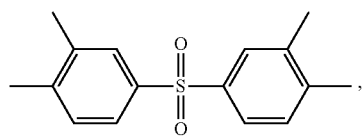

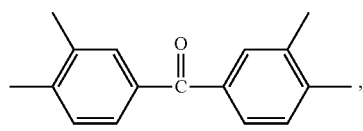

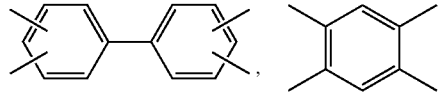

and mixtures thereof; $Y_1$ is selected from the group consisting of

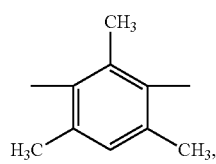

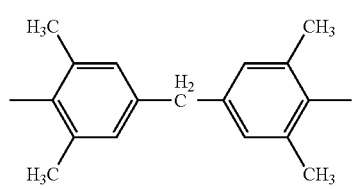

and mixtures thereof; $Y_2$ is selected from the group consisting of

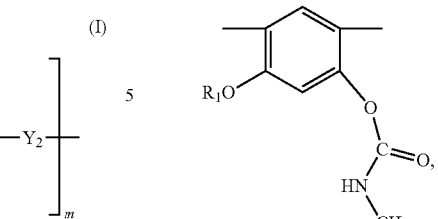

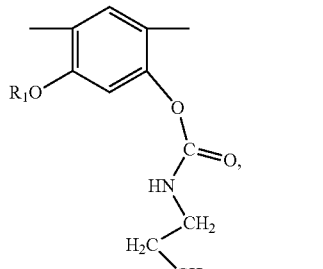

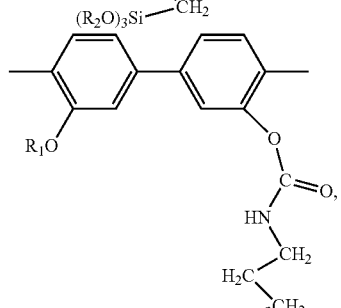

and mixtures thereof, and —$R_1$ is selected from the group consisting of

—H,   —COCH$_3$,   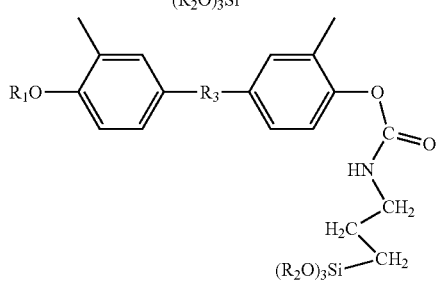

and mixtures thereof, and —$R_2$ is selected from the group consisting of

—CH$_3$, —C$_2$H$_5$ and —$R_3$ is selected from the group consisting of

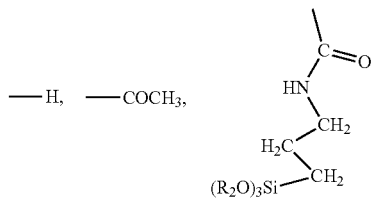

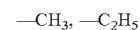

and mixtures thereof; n and m are independent integers from 2 to 500; the molar ratio of n/m is in a range of 1:10 to 10:1.

Within formula (I), preferably $X_1$ and $X_2$ are the same following group

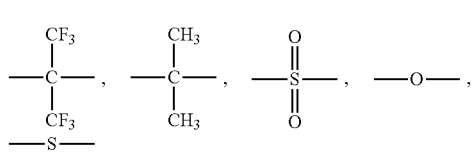

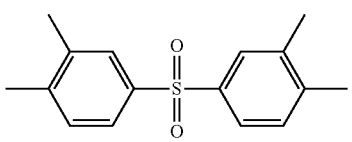

preferably $Y_1$ is

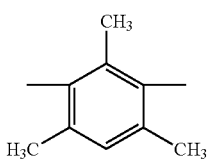

preferably $Y_2$ is

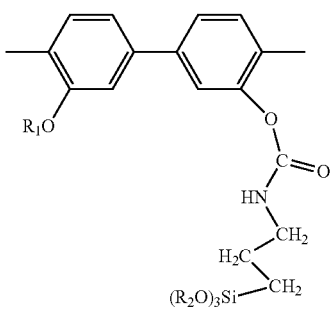

—$R_1$ is selected from the group consisting of

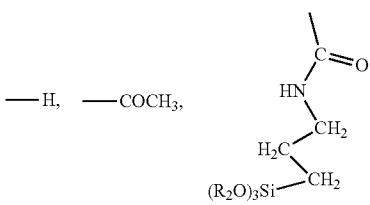

and preferably —$R_2$ is

—$CH_2CH_3$.

The new polyimide polymer with a plurality of repeating units of formula (I) that is used for making the high selectivity, high plasticization-resistant and solvent-resistant, both chemically and UV cross-linked polyimide membrane described in the current invention have a weight average molecular weight in the range of 50,000 to 1,000,000 Daltons, preferably between 70,000 to 500,000 Daltons.

The high selectivity, high plasticization-resistant and solvent-resistant, both chemically and UV cross-linked polyimide membrane in the present invention can be either asymmetric integrally skinned membrane or thin film composite (TFC) membrane.

The high selectivity, high plasticization-resistant and solvent-resistant, both chemically and UV cross-linked polyimide membrane described in the present invention can be fabricated into any convenient geometry such as flat sheet (or spiral wound), tube, or hollow fiber.

The asymmetric integrally-skinned flat sheet or hollow fiber high selectivity, high plasticization-resistant and solvent-resistant, both chemically and UV cross-linked polyimide membranes in the present invention was prepared by a phase inversion process, and then by applying a thin coating layer on the surface of the membrane.

The present invention provides a method for the preparation of high selectivity, high plasticization-resistant and solvent-resistant, both chemically and UV cross-linked polyimide membrane including: 1) preparing a casting solution of the new polyimide polymer with a plurality of repeating units of formula (I) by: a) dissolving 3-isocyanatopropyltrialkyloxysilane such as 3-isocyanatopropyltriethoxysilane and a polyimide polymer with a plurality of repeating units of formula (II) in an organic solvent such as N-methyl-2-pyrrolidone (NMP), 1,3-dioxolane, tetrahydrofuran (THF), and cyclohexanone to form a homogeneous solution; b) heating said homogeneous solution for 4-8 hours at 40-70° C. to form said solution of the new polyimide polymer with a plurality of repeating units of formula (I) via the reaction between 3-isocyanatopropyltrialkyloxysilane and polyimide polymer with a plurality of repeating units of formula (II); c) in some cases, some organic solvents such as hexane, n-octane, and n-decane that cannot dissolve the new polyimide polymer with a plurality of repeating units of formula (I) are added to said casting solution; 2) casting said casting solution of the new polyimide polymer with a plurality of repeating units of formula (I) on a membrane substrate or on a polymeric cloth substrate or on a clean glass plate to form a thin layer of said casting solution of the new polyimide polymer with a plurality of repeating units of formula (I); 3) removing the organic solvents from the thin layer of said casting solution of the new polyimide polymer with a plurality of repeating units of formula (I) to form a flat sheet membrane; 4) drying the membrane to form the chemically cross-linked polyimide membrane comprising the new polyimide polymer with a plurality of repeating units of formula (I) wherein the trialkyloxysilane groups have reacted with each other and have formed covalent bonds among the polymer chains; 5) coating said dried membrane with a thin layer of high permeability material such as a fluoropolymer or a UV radiation curable epoxy silicone; and 6) UV cross-linking said coated and dried membrane via UV radiation to further cross-link the membrane via covalent bonds between the UV cross-linkable sulfonyl or carbonyl group and methyl group on said new polyimide polymer chains with a plurality of repeating units of formula (I) to form said high selectivity, high plasticization-resistant and solvent-resistant, both chemically and UV cross-linked polyimide membrane.

The polyimide polymer used for the synthesis of the new polyimide polymer with a plurality of repeating units of formula (I) has a plurality of repeating units of formula (II):

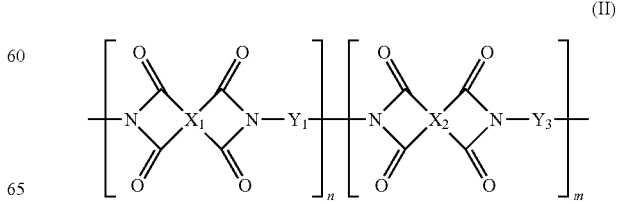

wherein $X_1$ is selected from the group consisting of

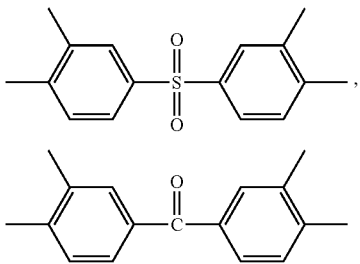

and mixtures thereof; wherein $X_2$ is selected from the group consisting of

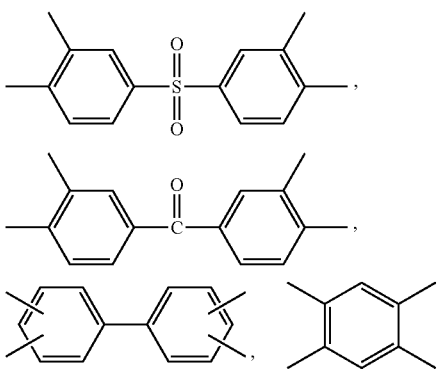

and mixtures thereof; $Y_1$ is selected from the group consisting of

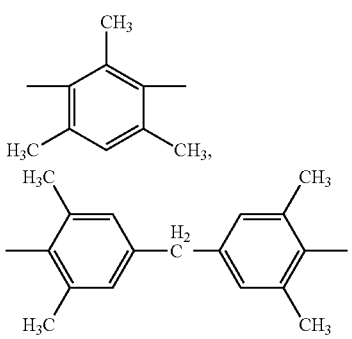

and mixtures thereof; $Y_3$ is selected from the group consisting of

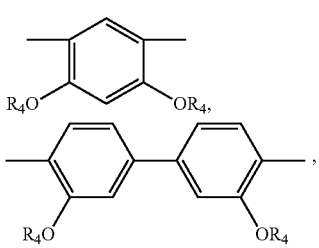

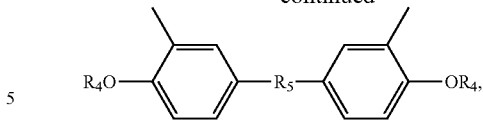

and mixtures thereof, and —$R_4$ is selected from the group consisting of —H, —COCH$_3$, and mixtures thereof, and —$R_5$ is selected from the group consisting of

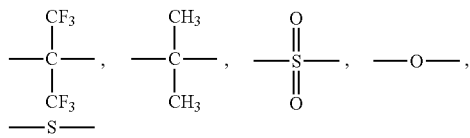

and mixtures thereof; n and m are independent integers from 2 to 500; the molar ratio of n/m is in a range of 1:10 to 10:1.

Within formula (II), preferably $X_1$ and $X_2$ are the same following group

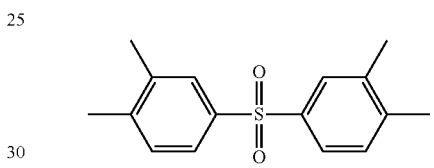

preferably $Y_1$ is

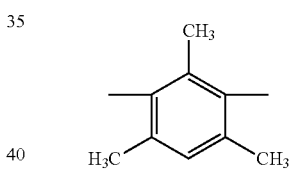

preferably $Y_3$ is

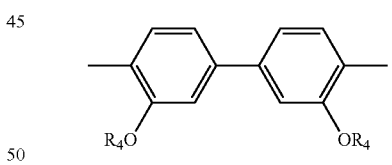

preferably —$R_4$ is a mixture of —H and —COCH$_3$.

The polyimide polymer with a plurality of repeating units of formula (II) that is used for synthesis of the new polyimide polymer with a plurality of repeating units of formula (I) described in the current invention have a weight average molecular weight in the range of 50,000 to 1,000,000 Daltons, preferably between 70,000 to 500,000 Daltons.

The thin film composite high selectivity, high plasticization-resistant and solvent-resistant, both chemically and UV cross-linked polyimide membrane described in the current invention comprises a thin nonporous selective separation layer formed from the new polyimide polymer with a plurality of repeating units of formula (I) described in the present invention and a porous nonselective mechanical support layer made from a material different from the new polyimide polymer with a plurality of repeating units of formula (I) described in the present invention. The thin film composite high selectivity, high plasticization-resistant and solvent-resistant, both chemically and UV cross-linked polyimide membrane described in the current invention has either hollow fiber or flat sheet geometry.

The porous nonselective mechanical support layer was made from a material different from the new polyimide polymer with a plurality of repeating units of formula (I) described in the present invention with a low selectivity and high flux. Selection of the porous nonselective mechanical support layer for the preparation of TFC high plasticization-resistant and solvent-resistant polymeric membrane in the present invention may be made on the basis of the heat resistance, solvent resistance, and mechanical strength of the porous nonselective mechanical support layer, as well as other factors dictated by the operating conditions for selective permeation. The porous nonselective mechanical support layer is preferably at least partially self-supporting, and in some instances may be essentially self-supporting. The porous nonselective mechanical support layer may provide essentially all of the structural support for the membrane. Some preferred polymers different from the new polyimide polymer with a plurality of repeating units of formula (I) that are suitable for the preparation of the porous nonselective mechanical support layer for the TFC high selectivity, high plasticization-resistant and solvent-resistant, both chemically and UV cross-linked polyimide membrane according to the present invention include, but are not limited to, polysulfones, sulfonated polysulfones, polyethersulfones (PESs), sulfonated PESs, polyethers, polyetherimides such as Ultem, cellulosic polymers such as cellulose acetate and cellulose triacetate, polyamides, polyimides such as P84 and P84HT, polyether ketones, and blends thereof.

The present invention provides another method for the preparation of high selectivity, high plasticization-resistant and solvent-resistant, both chemically and UV cross-linked polyimide thin film composite hollow fiber membrane including: 1) preparing a spinning sheath dope solution of the new polyimide polymer with a plurality of repeating units of formula (I) by: a) dissolving 3-isocyanatopropyltrialkyloxysilane such as 3-isocyanatopropyltriethoxysilane and a polyimide polymer with a plurality of repeating units of formula (II) in an organic solvent such as N-methyl-2-pyrrolidone (NMP), 1,3-dioxolane, tetrahydrofuran (THF), and cyclohexanone to form a homogeneous solution; b) heating said homogeneous solution for 24-72 hours at 40-70° C. to form said spinning solution of the new polyimide polymer with a plurality of repeating units of formula (I) via the reaction between 3-isocyanatopropyltrialkyloxysilane and polyimide polymer with a plurality of repeating units of formula (II); c) in some cases, some organic solvents such as hexane, n-octane, and n-decane that cannot dissolve the new polyimide polymer with a plurality of repeating units of formula (I) are added to said spinning solution; 2) preparing a core dope solution of a cheap polymer such as polyethersulfone; 3) spinning said sheath dope solution of the new polyimide polymer with a plurality of repeating units of formula (I) and said core dope solution simultaneously in the presence of a bore fluid such as a mixture of NMP and water using a triple-annulus spinneret to form a nascent TFC hollow fiber membrane with a thin sheath layer of said sheath dope solution of the new polyimide polymer with a plurality of repeating units of formula (I); 4) removing the organic solvents from the nascent TFC hollow fiber membrane; 5) drying the membrane to form said TFC hollow fiber membrane comprising the new polyimide polymer with a plurality of repeating units of formula (I) wherein the trialkyloxysilane groups have reacted with each other and have formed covalent bonds among the polymer chains; 6) coating said dried TFC hollow fiber membrane with a thin layer of high permeability material such as a fluoropolymer or a UV radiation curable epoxy silicone; and 7) UV cross-linking said coated and dried TFC hollow fiber membrane via UV radiation to cross-link the membrane via covalent bonds between the UV cross-linkable sulfonyl or carbonyl group and methyl group on said new polyimide polymer chains with a plurality of repeating units of formula (I) to form said high selectivity, high plasticization-resistant and solvent-resistant, both chemically and UV cross-linked polyimide thin film composite hollow fiber membrane.

The invention provides a process for separating at least one gas from a mixture of gases using the high selectivity, high plasticization-resistant and solvent-resistant, both chemically and UV cross-linked polyimide membrane described in the present invention, the process comprising: (a) providing a both chemically and UV cross-linked polyimide membrane described in the present invention which is permeable to said at least one gas; (b) contacting the mixture on one side of the both chemically and UV cross-linked polyimide membrane described in the present invention to cause said at least one gas to permeate the membrane; and (c) removing from the opposite side of the membrane a permeate gas composition comprising a portion of said at least one gas which permeated said membrane.

The high selectivity, high plasticization-resistant and solvent-resistant, both chemically and UV cross-linked polyimide membrane described in the present invention is especially useful in the purification, separation or adsorption of a particular species in the liquid or gas phase. In addition to separation of pairs of gases, the high selectivity, high plasticization-resistant and solvent-resistant, both chemically and UV cross-linked polyimide membrane described in the present invention may, for example, be used for the desalination of water by reverse osmosis or for the separation of proteins or other thermally unstable compounds, e.g. in the pharmaceutical and biotechnology industries. The high selectivity, high plasticization-resistant and solvent-resistant, both chemically and UV cross-linked polyimide membrane described in the present invention may also be used in fermenters and bioreactors to transport gases into the reaction vessel and transfer cell culture medium out of the vessel. Additionally, the high selectivity, high plasticization-resistant and solvent-resistant, both chemically and UV cross-linked polyimide membrane described in the present invention may be used for the removal of microorganisms from air or water streams, water purification, ethanol production in a continuous fermentation/membrane pervaporation system, and in detection or removal of trace compounds or metal salts in air or water streams.

The high selectivity, high plasticization-resistant and solvent-resistant, both chemically and UV cross-linked polyimide membrane described in the present invention is especially useful in gas separation processes in air purification, petrochemical, refinery, and natural gas industries. Examples of such separations include separation of volatile organic compounds (such as toluene, xylene, and acetone) from an atmospheric gas, such as nitrogen or oxygen and nitrogen recovery from air. Further examples of such separations are for the separation of He, $CO_2$ or $H_2S$ from natural gas, $H_2$ from $N_2$, $CH_4$, and Ar in ammonia purge gas streams, $H_2$ recovery in refineries, olefin/paraffin separations such as propylene/propane separation, xylene separations, iso/normal paraffin separations, liquid natural gas separations, C2+ hydrocarbon recovery. Any given pair or group of gases that differ in molecular size, for example nitrogen and oxygen, carbon dioxide and methane, hydrogen and methane or carbon monoxide, helium and methane, can be separated using the high selectivity, high plasticization-resistant and solvent-resistant, both chemically and UV cross-linked polyimide membrane described in the present invention. More than two gases can be removed from a third gas. For example, some of the gas components which can be selectively removed from a raw natural gas using the high selectivity, high plasticization-resistant and solvent-resistant, both chemically and UV cross-linked polyimide membrane described herein include carbon dioxide, oxygen, nitrogen, water vapor, hydrogen sulfide, helium, and other trace gases. Some of the gas components that can be selectively retained include hydrocarbon gases. When permeable components are acid components selected from the group consisting of carbon dioxide, hydrogen sulfide, and mixtures thereof and are removed from a hydrocarbon mixture such as natural gas, one module, or at least two in parallel service, or a series of modules may be utilized to remove the acid components. For example, when one module is utilized, the pressure of the feed gas may vary from 275 kPa to about 2.6 MPa (25 to 4000 psi). The differential pressure across the membrane can be as low as about 70 kPa or as high as 14.5 MPa (about 10 psi or as high as about 2100 psi) depending on many factors such as the particular membrane used, the flow rate of the inlet stream and the availability of a compressor to compress the permeate stream if such compression is desired. Differential pressure greater than about 14.5 MPa (2100 psi) may rupture the membrane. A differential pressure of at least 0.7 MPa (100 psi) is preferred since lower differential pressures may require more modules, more time and compression of intermediate product streams. The operating temperature of the process may vary depending upon the temperature of the feed stream and upon ambient temperature conditions. Preferably, the effective operating temperature of the membranes of the present invention will range from about −50° to about 150° C. More preferably, the effective operating temperature of the high selectivity, high plasticization-resistant and solvent-resistant, both chemically and UV cross-linked polyimide membrane of the present invention will range from about −20° to about 100° C., and most preferably, the effective operating temperature of the membranes of the present invention will range from about 25° to about 100° C.

The high selectivity, high plasticization-resistant and solvent-resistant, both chemically and UV cross-linked polyimide membrane described in the present invention are also especially useful in gas/vapor separation processes in chemical, petrochemical, pharmaceutical and allied industries for removing organic vapors from gas streams, e.g. in off-gas treatment for recovery of volatile organic compounds to meet clean air regulations, or within process streams in production plants so that valuable compounds (e.g., vinyl-chloride monomer, propylene) may be recovered. Further examples of gas/vapor separation processes in which the high selectivity, high plasticization-resistant and solvent-resistant, both chemically and UV cross-linked polyimide membrane described in the present invention may be used are hydrocarbon vapor separation from hydrogen in oil and gas refineries, for hydrocarbon dew pointing of natural gas (i.e. to decrease the hydrocarbon dew point to below the lowest possible export pipeline temperature so that liquid hydrocarbons do not separate in the pipeline), for control of methane number in fuel gas for gas engines and gas turbines, and for gasoline recovery. The high selectivity, high plasticization-resistant and solvent-resistant, both chemically and UV cross-linked polyimide membrane described in the present invention may incorporate a species that adsorbs strongly to certain gases (e.g. cobalt porphyrins or phthalocyanines for $O_2$ or silver (I) for ethane) to facilitate their transport across the membrane.

The high selectivity, high plasticization-resistant and solvent-resistant, both chemically and UV cross-linked polyimide membrane described in the present invention also has immediate application to concentrate olefin in a paraffin/olefin stream for olefin cracking application. For example, the high selectivity, high plasticization-resistant and solvent-resistant, both chemically and UV cross-linked polyimide membrane described in the present invention can be used for propylene/propane separation to increase the concentration of the effluent in a catalytic dehydrogenation reaction for the production of propylene from propane and isobutylene from isobutane. Therefore, the number of stages of a propylene/propane splitter that is required to get polymer grade propylene can be reduced. Another application for the high selectivity, high plasticization-resistant and solvent-resistant, both chemically and UV cross-linked polyimide membrane described in the present invention is for separating isoparaffin and normal paraffin in light paraffin isomerization and MaxEne™, a process for enhancing the concentration of normal paraffin (n-paraffin) in the naphtha cracker feedstock, which can be then converted to ethylene.

The high selectivity, high plasticization-resistant and solvent-resistant, both chemically and UV cross-linked polyimide membrane described in the present invention can also be operated at high temperature to provide the sufficient dew point margin for natural gas upgrading (e.g, $CO_2$ removal from natural gas). The high selectivity, high plasticization-resistant and solvent-resistant, both chemically and UV cross-linked polyimide membrane described in the present invention can be used in either a single stage membrane or as the first or/and second stage membrane in a two stage membrane system for natural gas upgrading.

The high selectivity, high plasticization-resistant and solvent-resistant, both chemically and UV cross-linked polyimide membrane described in the present invention may also be used in the separation of liquid mixtures by pervaporation, such as in the removal of organic compounds (e.g., alcohols, phenols, chlorinated hydrocarbons, pyridines, ketones) from water such as aqueous effluents or process fluids. A membrane which is ethanol-selective would be used to increase the ethanol concentration in relatively dilute ethanol solutions (5-10% ethanol) obtained by fermentation processes. Another liquid phase separation example using the high selectivity, high plasticization-resistant and solvent-resistant, both chemically and UV cross-linked polyimide membrane described in the present invention is the deep desulfurization of gasoline and diesel fuels by a pervaporation membrane process similar to the process described in U.S. Pat. No. 7,048,846, incorporated by reference herein in its entirety. The high selectivity, high plasticization-resistant and solvent-resistant, both chemically and UV cross-linked polyimide membrane described in the present invention that are selective to sulfur-containing molecules would be used to selectively remove sulfur-containing molecules from fluid catalytic cracking (FCC) and other naphtha hydrocarbon streams. Further liquid phase examples include the separation of one organic component from another organic component, e.g. to separate isomers of organic compounds. Mixtures of organic compounds which may be separated using the high selectivity, high plasticization-resistant and solvent-resistant, both chemically and UV cross-linked polyimide membrane described in the present invention include: ethylacetate-ethanol, diethylether-ethanol, acetic acid-ethanol, benzene-ethanol, chloroform-ethanol, chloroform-methanol, acetone-isopropylether, allylalcohol-allylether, allylalcohol-cyclohexane, butanol-butylacetate, butanol-1-butylether, ethanol-ethylbutylether, propylacetate-propanol, isopropylether-isopropanol, methanol-ethanol-isopropanol, and ethylacetate-ethanol-acetic acid.

EXAMPLES

The following examples are provided to illustrate one or more preferred embodiments of the invention, but are not limited embodiments thereof. Numerous variations can be made to the following examples that lie within the scope of the invention.

Example 1

Preparation of Chemically Cross-Linked DSDA-TMPDA-HAB-ICPTESi Polyimide Dense Film Membrane and Both Chemically and UV Cross-Linked DSDA-TMPDA-HAB-ICPTESi Polyimide Dense Film Membrane 7.0 g of poly(DSDA-TMPDA-HAB) polyimide synthesized from polycondensation reaction of 3,3',4,4'-diphenylsulfone tetracarboxylic dianhydride (DSDA) with a mixture of 2,4,6-trimethyl-m-phenylenediamine (TMPDA) and 3,3'-dihydroxy-4,4'-diamino-biphenyl (HAB) (TMPDA/HAB=2:1 molar ratio) was dissolved in 30.0 g of anhydrous NMP solvent. The mixture was mechanically stirred for 2 hours to form a homogeneous solution. 0.74 g of 3-isocyanatopropyltriethoxysilane (ICPTESi) was added to the poly(DSDA-TMPDA-HAB) polyimide solution. The solution was mechanically stirred for 4 hours at 65° C. to allow the hydroxyl groups on poly(DSDA-TMPDA-HAB) polymer chain to react with the isocyanate groups on ICPTESi to form covalent bonds. The resulting homogeneous casting dope was allowed to degas overnight. The chemically cross-linked DSDA-TMPDA-HAB-ICPTESi polyimide dense film membrane was prepared from the bubble free casting dope on a clean glass plate using a doctor knife with an 18-mil gap. The dense film membrane together with the glass plate was heated at 60° C. for 12 hours on top of a hot plate. The solvents were removed slowly, The dense film membrane was then heated at 200° C. under vacuum for 48 hours to completely remove the residual solvent. The chemically cross-linked DSDA-TMPDA-HAB-ICPTESi polyimide dense film membrane was then further UV cross-linked under UV radiation for 25 minutes to form the both chemically and UV cross-linked DSDA-TMPDA-HAB-ICPTESi polyimide dense film membrane.

Example 2

Evaluation of $CO_2/CH_4$, $H_2/CH_4$, and $He/CH_4$ Separation Performance of Chemically Cross-Linked DSDA-TMPDA-HAB-ICPTESi and Both Chemically and UV Cross-Linked DSDA-TMPDA-HAB-ICPTESi Dense Film Membranes The chemically cross-linked DSDA-TMPDA-HAB-ICPTESi and both chemically and UV cross-linked DSDA-TMPDA-HAB-ICPTESi dense film membranes were tested for $CO_2/CH_4$, $H_2/CH_4$, and $He/CH_4$ separations at 50° C. under 791 kPa (100 psig) single feed gas pressure for $CO_2$, $H_2$, $CH_4$, and He gases. The results are shown in Table 1. It can be seen from Table 1 that the both chemically and UV cross-linked DSDA-TMPDA-HAB-ICPTESi dense film membrane showed very high selectivities for $CO_2/CH_4$, $H_2/CH_4$, and $He/CH_4$ separations and the selectivities are much higher than the only chemically cross-linked DSDA-TMPDA-HAB-ICPTESi dense film membrane.

TABLE 1

$CO_2/CH_4$, $H_2/CH_4$, and $He/CH_4$ separation performance of chemically cross-linked DSDA-TMPDA-HAB-ICPTESi and both chemically and UV cross-linked DSDA-TMPDA-HAB-ICPTESi dense film membranes

| Dense film membrane | $P_{CO2}$ (Barrer) | $\alpha_{CO2/CH4}$ | $P_{H2}$ (Barrer) | $\alpha_{H2/CH4}$ | $P_{He}$ (Barrer) | $\alpha_{He/CH4}$ |
|---|---|---|---|---|---|---|
| Chemically cross-linked DSDA-TMPDA-HAB-ICPTESi | 15.6 | 18.1 | 32.4 | 37.8 | — | — |
| Chemically and UV cross-linked DSDA-TMPDA-HAB-ICPTESi | 7.22 | 42.5 | 41.8 | 245.9 | 41.4 | 243.4 |

1 Barrer = $10^{-10}$ cm$^3$ (STP) · cm/cm$^2$ s (cm Hg)
Testing conditions: 50° C., 791 kPa (100 psig) single feed gases.

Example 3

Evaluation of $CO_2$ Plasticization Resistance of both Chemically and UV Cross-linked DSDA-TMPDA-HAB-ICPTESi Dense Film Membrane To study the effect of both chemical and UV cross-linking on the plasticization resistance of DSDA-TMPDA-HAB-ICPTESi dense film membrane, the both chemically and UV cross-linked DSDA-TMPDA-HAB-ICPTESi dense film membrane was conditioned with $CO_2$ at different pressures. The change of $CO_2$ relative permeability with the increase of the applied $CO_2$ pressure at 50° C. was studied. It can be seen from Table 2 that no $CO_2$ plasticization was observed up to 4928 kPa (700 psig) pure $CO_2$ pressure for the both chemically and UV cross-linked DSDA-TMPDA-HAB-ICPTESi dense film membrane. The high $CO_2$ plasticization resistance of the both chemically and UV cross-linked DSDA-TMPDA-HAB-ICPTESi dense film membrane is mainly attributed to the chemical and UV cross-linking and formation of rigid covalently interpolymer-chain-connected cross-linked networks.

TABLE 2

Study on CO$_2$ plasticization resistance of both chemically and UV cross-linked DSDA-TMPDA-HAB-ICPTESi dense film membrane

| CO$_2$ pressure (psig) | P$_{CO2,p}$/P$_{CO2,100\ psig}$ |
|---|---|
| 100 | 1 |
| 300 | 0.86 |
| 500 | 0.81 |
| 700 | 0.86 |

P$_{CO2,p}$/P$_{CO2,100\ psig}$ is the ratio of the CO$_2$ permeability at p CO$_2$ pressure to the CO$_2$ permeability at 100 psig CO$_2$ pressure;
Testing conditions: 50° C., single CO$_2$ feed gas.

Example 4

Preparation of Chemically and UV Cross-Linked TFC DSDA-TMPDA-HAB-ICPTESi Polyimide Hollow Fiber Membrane The chemically and UV cross-linked TFC DSDA-TMPDA-HAB-ICPTESi polyimide hollow fiber membrane comprising a chemically and UV cross-linked TFC DSDA-TMPDA-HAB-ICPTESi polyimide sheath layer is fabricated via a co-extrusion phase inversion spinning process from a sheath dope and a core dope using a triple-orifice spinneret. The core dope comprises polyethersulfone (PES) polymer, P84 polyimide, NMP, LiNO$_3$ and lactic acid was prepared. The sheath dope comprises poly(DSDA-TMPDA-HAB) polyimide, ICPTESi, NMP, 1,3-dioxolane, isopropanol, and methylethylketone was also prepared. The core dope and sheath dope were co-extruded through a triple-orifice spinneret at 50° C. A bore fluid containing 20% by weight of water in NMP was injected to the bore of the fiber simultaneously with the co-extruding of the core dope and sheath dope. The ratio of the core dope flow rate, the sheath dope flow rate, and the bore fluid flow rate was 10:1:2.7. The nascent fiber traveled through an air gap length of 13 cm at room temperature, and then was immersed into a water coagulant bath at 0° C. and wound up at a rate of 23 m/min. The water-wet fiber was annealed in a hot water bath at 85° C. for 30 minutes. The annealed water-wet fiber was then sequentially exchanged with methanol and hexane for three times and for 30 minutes each time, followed by drying at 85° C. in an oven for 1 hour to form dried TFC hollow fiber membrane. The dried chemically cross-linked DSDA-TMPDA-HAB-ICPTESi TFC hollow fiber membrane was coated with a thin layer of an UV curable epoxysilicone SilForce* UV9315 purchased from Momentive in the presence of a bis(dodecylphenyl)iodonium salt photocatalyst SilForce* UV9380C purchased from Momentive. Both the UV9315 coating layer and the chemically cross-linked DSDA-TMPDA-HAB-ICPTESi polyimide sheath layer were UV cross-linked under UV radiation for 3 minutes to form the high selectivity, high plasticization-resistant and solvent-resistant, both chemically and UV cross-linked DSDA-TMPDA-HAB-ICPTESi TFC hollow fiber membrane.

The invention claimed is:

1. A polymer comprising a plurality of repeating units of formula (I):

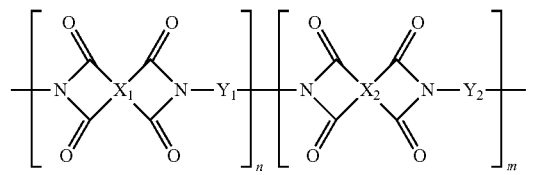

wherein X$_1$ is selected from the group consisting of

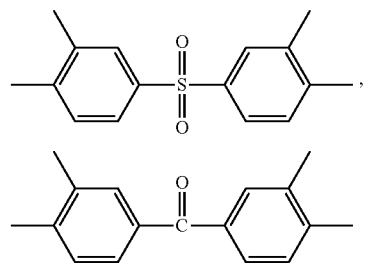

and mixtures thereof; wherein X$_2$ is selected from the group consisting of

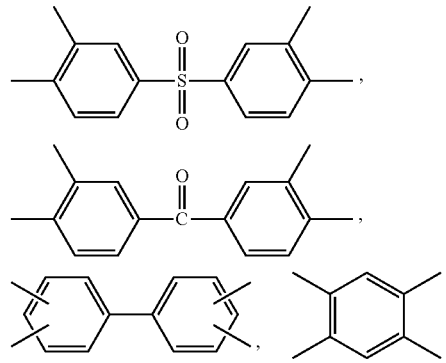

and mixtures thereof; Y$_1$ is selected from the group consisting of

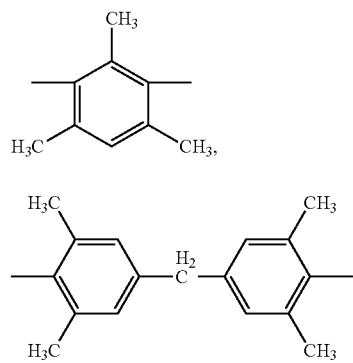

and mixtures thereof; Y$_2$ is selected from the group consisting of

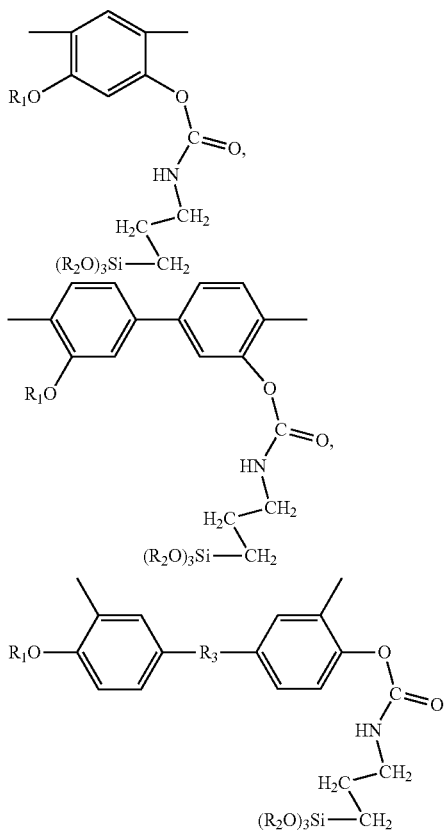

and mixtures thereof, and —R$_1$ is selected from the group consisting of

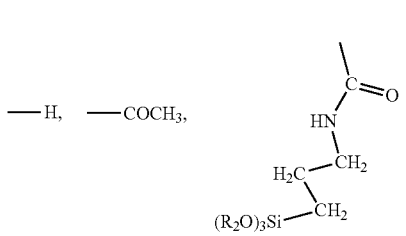

and mixtures thereof, and —R$_2$ is selected from the group consisting of

—CH$_3$, —C$_2$H$_5$ and —R$_3$ is selected from the group consisting of

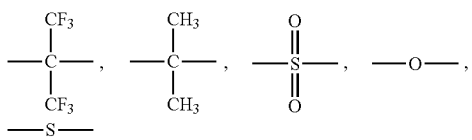

and mixtures thereof; n and m are independent integers from 2 to 500; the molar ratio of n/m is in a range of 1:10 to 10:1.

2. The polyimide polymer of claim 1 wherein X$_1$ and X$_2$ are the same and are

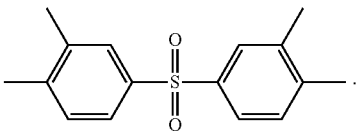

3. The polyimide polymer of claim 1 wherein Y$_1$ is

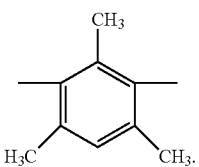

4. The polyimide polymer of claim 1 wherein Y$_2$ is

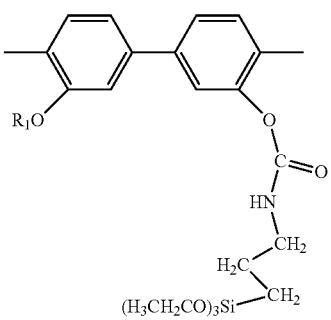

and —R$_1$ is selected from the group consisting of

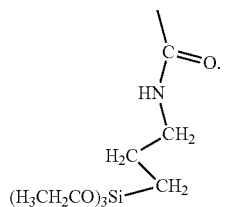

5. A polyimide polymer membrane comprising the polyimide polymer of claim 1.

6. The polyimide polymer membrane of claim 5 is chemically and UV cross-linked.

7. The polyimide polymer membrane of claim 5 comprising a thin nonporous selective separation layer formed from the polyimide polymer with a plurality of repeating units of formula (I) and a porous nonselective mechanical support layer made from a material different from the polyimide polymer with a plurality of repeating units of formula (I).

8. The polyimide polymer membrane of claim 7 wherein said thin nonporous selective separation layer formed from the polyimide polymer with a plurality of repeating units of formula (I) is chemically and UV cross-linked.

9. The polyimide polymer membrane of claim 7 wherein said material different from the polyimide polymer with a plurality of repeating units of formula (I) is selected from the group consisting of polysulfones, sulfonated polysulfones, polyethersulfones (PESs), sulfonated PESs, polyethers, polyetherimides, cellulosic polymers, polyamides, polyimides, polyether ketones, and blends thereof.

10. A method of making a chemically and UV cross-linked polyimide membrane comprising: 1) preparing a casting solution of a polyimide polymer with a plurality of repeating units of a formula (I):

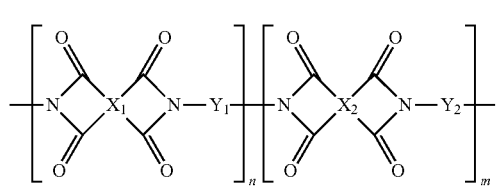

wherein $X_1$ is selected from the group consisting of

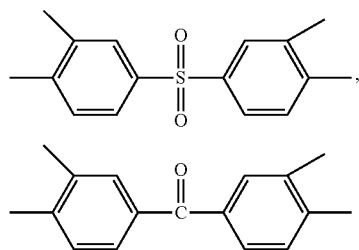

and mixtures thereof, wherein $X_2$ is selected from the group consisting of

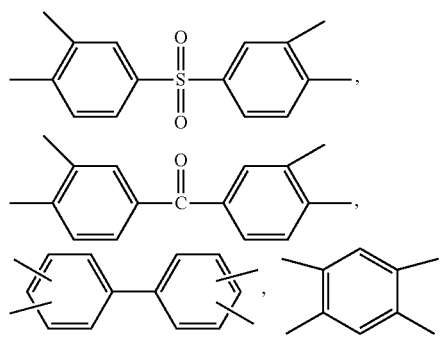

and mixtures thereof; $Y_1$ is selected from the group consisting of

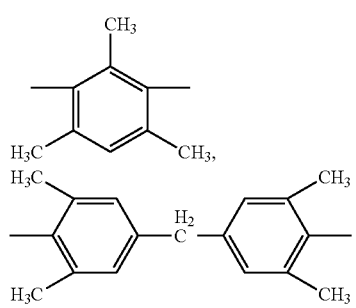

and mixtures thereof; $Y_2$ is selected from the group consisting of

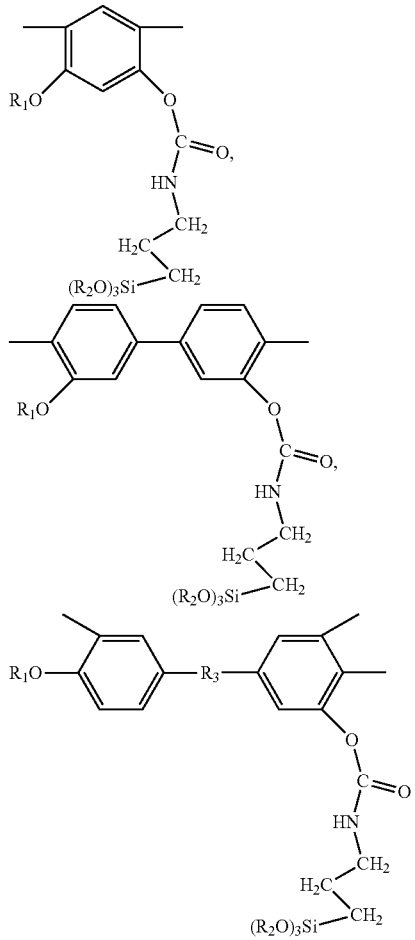

and mixtures thereof, and $-R_1$ is selected from the group consisting of

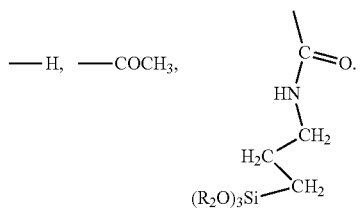

and mixtures thereof, and $-R_2$ is selected from the group consisting of $-CH_3$, $-C_2H_5$ and $-R_3$ is selected from the group consisting of

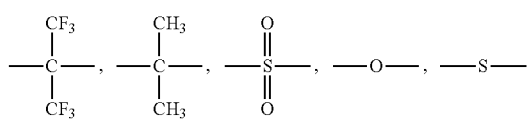

and mixtures thereof; n and m are independent integers from 2 to 500; the molar ratio of n/m is in a range of 1:10 to 10:1 by: a) dissolving 3-isocyanatopropyltrialkyloxysilane and a polyimide polymer with a plurality of repeating units of formula (II)

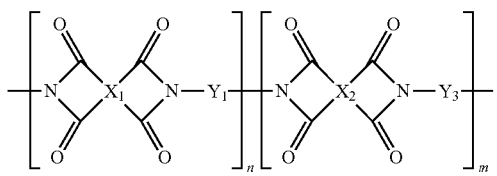
(II)

wherein $X_1$ is selected from the group consisting of

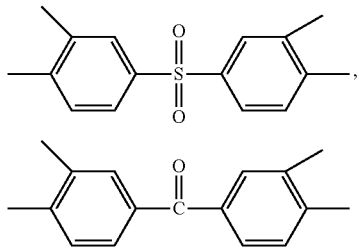

and mixtures thereof; wherein $X_2$ is selected from the group consisting of

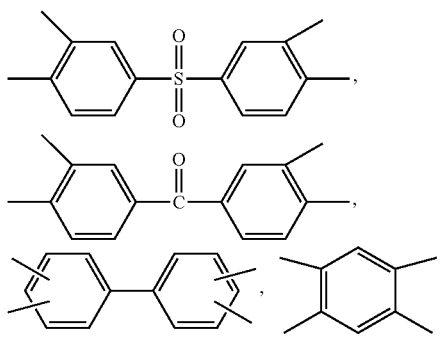

and mixtures thereof; $Y_1$ is selected from the group consisting of

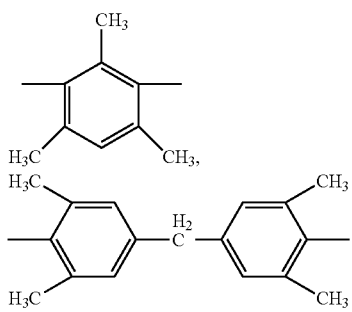

and mixtures thereof; $Y_3$ is selected from the group consisting of

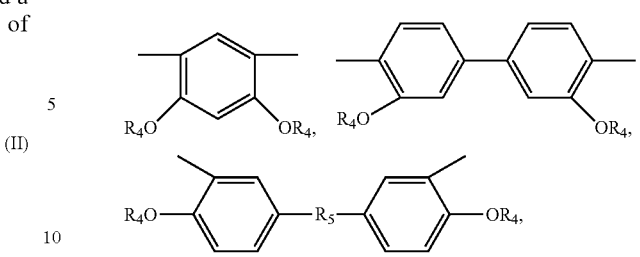

and mixtures thereof, and —$R_4$ is selected from the group consisting of —H, —COCH$_3$, and mixtures thereof, and —$R_5$ is selected from the group consisting of

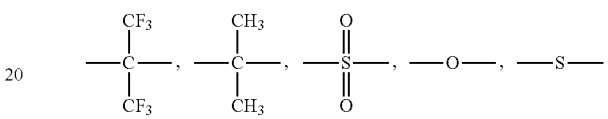

and mixtures thereof; n and m are independent integers from 2 to 500; the molar ratio of n/m is in a range of 1:10 to 10 in an organic solvent to form a homogeneous solution; b) heating said homogeneous solution for 4-8 hours at 40-70° C. to form said solution of the polyimide polymer via a reaction between 3-isocyanatopropyltrialkyloxysilane and said polyimide polymer with a plurality of repeating units of formula (II); 2) casting said casting solution of the polyimide polymer with a plurality of repeating units of formula (I) on a membrane substrate or on a polymeric cloth substrate or on a clean glass plate to form a thin layer of said casting solution of the polyimide polymer with a plurality of repeating units of formula (I); 3) removing the organic solvents from the thin layer of said casting solution of the polyimide polymer to form a flat sheet membrane; 4) drying the membrane to form chemically cross-linked polyimide membrane comprising the polyimide polymer with a plurality of repeating units of formula (I) wherein the trialkyloxysilane groups have reacted with each other and have formed covalent bonds among the polymer chains; 5) coating said dried membrane with a thin layer of high permeability material; and 6) UV cross-linking said coated and dried membrane via UV radiation to cross-link the membrane via covalent bonds between the UV cross-linkable sulfonyl or carbonyl group and methyl group on said new polyimide polymer chains with a plurality of repeating units of formula (I).

11. The method of claim 10 wherein the organic solvent is selected from the group consisting of N-methyl-2-pyrrolidone, 1,3-dioxolane, tetrahydrofuran, and cyclohexanone.

12. The method of claim 10 wherein an organic solvents that cannot dissolve the new polyimide polymer with a plurality of repeating units of formula (I) is added to said casting solution.

13. A process for separating at least one gas from a mixture of gases using a high selectivity, high plasticization-resistant and solvent-resistant, both chemically and UV cross-linked polyimide membrane the process comprising: (a) providing a both chemically and UV cross-linked polyimide membrane prepared from a polyimide polymer with a plurality of repeating units of a formula (I):

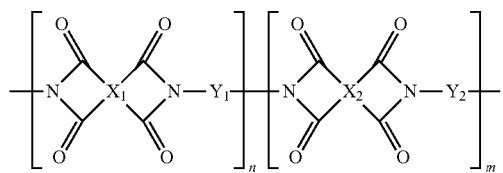
(I)

wherein $X_1$ is selected from the group consisting of

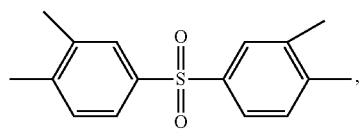

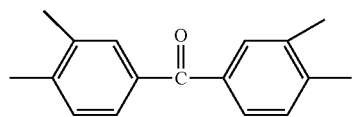

and mixtures thereof; wherein $X_2$ is selected from the group consisting of

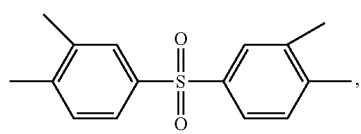

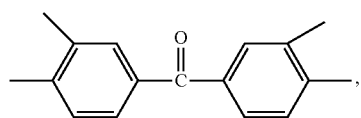

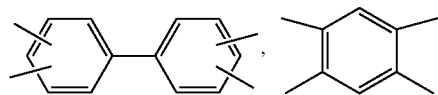

and mixtures thereof; $Y_1$ is selected from the group consisting of

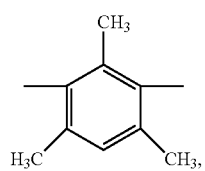

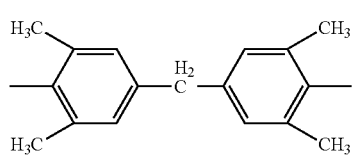

and mixtures thereof; $Y_2$ is selected from the group consisting of

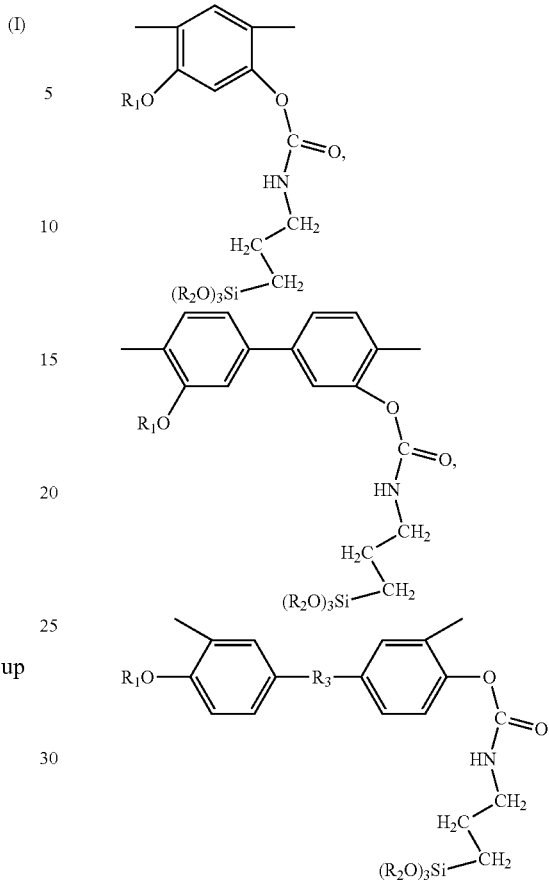

and mixtures thereof, and —$R_1$ is selected from the group consisting of

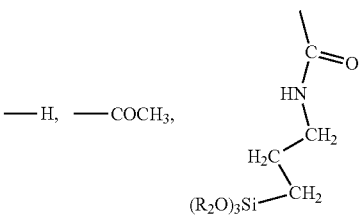

and mixtures thereof, and —$R_2$ is selected from the group consisting of

—$CH_3$, —$C_2H_5$ and —$R_3$ is selected from the group consisting of

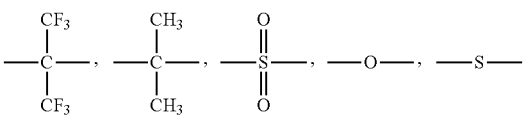

and mixtures thereof; n and m are independent integers from 2 to 500; the molar ratio of n/m is in a range of 1:10 to 10:1 wherein said polyimide membrane is permeable to said at least one gas; (b) contacting the mixture on one side of the polyimide membrane to cause said at least one gas to permeate the membrane; and (c) removing from the opposite side of the membrane a permeate gas composition comprising a portion of said at least one gas which permeated said membrane.

14. The process of claim 13 wherein said gases comprise volatile organic compounds in air.

15. The process of claim 13 wherein said gases comprise a mixture of helium, carbon dioxide or hydrogen sulfide in natural gas.

16. The process of claim 13 wherein said gases comprise hydrogen in a mixture of hydrocarbon gases from a refinery.

17. The process of claim 13 wherein said gases comprise a mixture of olefins and paraffins.

18. A process for separating a liquid mixture comprising sending said liquid mixture to a high selectivity, high plasticization-resistant and solvent-resistant, both chemically and UV cross-linked polyimide membrane wherein the both chemically and UV cross-linked polyimide membrane is prepared from a polyimide polymer with a plurality of repeating units of a formula (I):

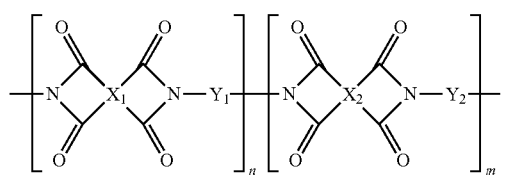

wherein $X_1$ is selected from the group consisting of

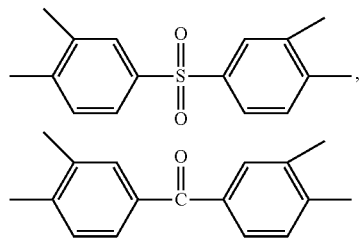

and mixtures thereof; wherein $X_2$ is selected from the group consisting of

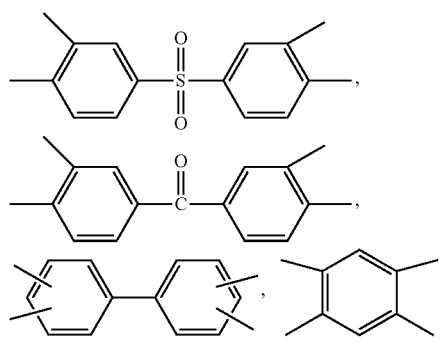

and mixtures thereof; $Y_1$ is selected from the group consisting of

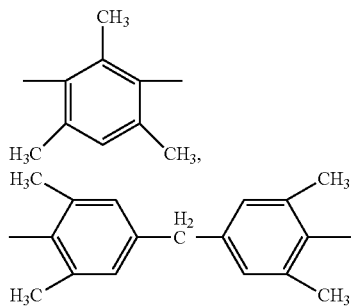

and mixtures thereof; $Y_2$ is selected from the group consisting of

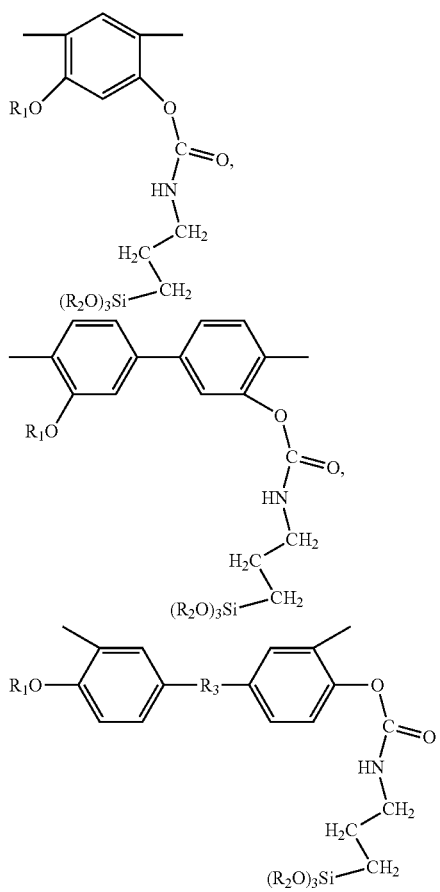

and mixtures thereof, and —$R_1$ is selected from the group consisting of

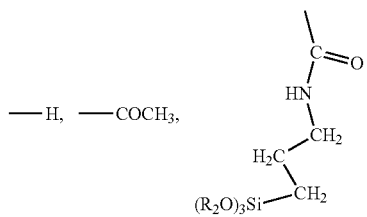

and mixtures thereof, and —R$_2$ is selected from the group consisting of

—CH$_3$, —C$_2$H$_5$ and —R$_3$ is selected from the group consisting of

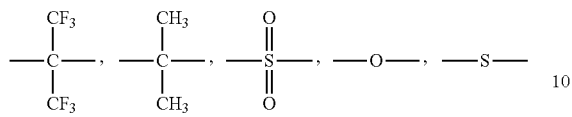

and mixtures thereof; n and m are independent integers from 2 to 500; the molar ratio of n/m is in a range of 1:10 to 10:1 wherein said polyimide membrane is permeable to said at least one component of said liquid; (b) contacting the liquid mixture on one side of the polyimide membrane to cause said at least one liquid to permeate the membrane; and (c) removing from the opposite side of the membrane a permeate liquid composition comprising a portion of said at least one liquid which permeated said membrane.

19. The process of claim 18 wherein said liquid mixture comprises at least one organic compound in water.

20. The process of claim 19 wherein said organic compounds are selected from the group consisting of alcohols, phenols, chlorinated hydrocarbons, pyridines, and ketones.

21. The process of claim 18 wherein said liquid mixture comprises a fermentation product comprising ethanol.

22. The process of claim 18 wherein said liquid mixture comprises gasoline or diesel fuel.

* * * * *